United States Patent [19]

Selby

[11] Patent Number: 4,852,584

[45] Date of Patent: Aug. 1, 1989

[54] FLUID COLLECTION TUBE WITH A SAFETY FUNNEL AT ITS OPEN END

[76] Inventor: Charles R. Selby, 1710 F Rd., Delta, Colo. 81416

[21] Appl. No.: 256,598

[22] Filed: Oct. 11, 1988

[51] Int. Cl.[4] ............ A61B 5/00

[52] U.S. Cl. ............ 128/760; 604/403

[58] Field of Search ............ 128/760, 763, 764; 604/403, 415

[56] References Cited

U.S. PATENT DOCUMENTS

| | | | |
|---|---|---|---|
| 3,811,136 | 5/1974 | Whitney et al. | 128/760 |
| 3,902,477 | 9/1975 | Gerarde | 604/403 |
| 3,923,040 | 12/1975 | Beach | 128/760 |
| 4,116,066 | 9/1978 | Mehl et al. | 128/760 |
| 4,335,730 | 6/1982 | Griffin | 128/760 |
| 4,761,379 | 8/1988 | Williams et al. | 128/760 |
| 4,791,938 | 12/1988 | Van Valkenburg | 604/403 |

FOREIGN PATENT DOCUMENTS

| | | | |
|---|---|---|---|
| 0399702 | 10/1933 | United Kingdom | 604/403 |

*Primary Examiner*—Max Hindenburg
*Attorney, Agent, or Firm*—Donald W. Erickson

[57] ABSTRACT

A medical safety device which reduces the risk of transmitting disease to health care personnel who take or handle body fluid samples such as blood samples. The device reduces the risk of the transmission of disease caused by needlestick and accidental spillage of fluid samples. The device comprises a funnel shaped needle guard having a neck portion which fits snugly over the end of a sample tube such as a vacuum tube. The glass sample tube is coated with a resin to make it substantially shatterproof. The interior surface of the needle guard has interconnecting vertical and circular grooves to channel accidentally spilled fluid into the tube.

5 Claims, 2 Drawing Sheets

FLUID COLLECTION TUBE WITH A SAFETY FUNNEL AT ITS OPEN END

BACKGROUND OF THE INVENTION

This invention relates to improvements in medical safety devices. More particularly, the invention is directed at devices for improving the safety of health care personnel who are exposed to the spread of disease when taking blood samples, handling the blood samples and performing chemical analysis of blood samples. In the taking of a blood sample using a hypodermic syringe, accidental needlesticks can occur. This is a serious problem because the needlestick can spread disease such as hepatitis, venereal diseases, AIDS, and the like. The device of the present invention reduces the possibility of accidental needlestick during transfer of the blood sample to a vial or tube. In addition, the device of the present invention reduces the possibility of accidental spillage of the blood sample during transfer of the sample to a vial or tube. In another aspect of the present invention, there is provided means for safely containing the blood sample within the vial or tube in the event it is accidentally dropped.

SUMMARY OF THE INVENTION

The present invention relates to improvements in a medical safety device which is used in obtaining and transporting blood samples or samples of other body fluids. Briefly stated, the medical safety device of the present invention comprises a funnel shaped needle guard and a resin coated glass sample tube, said guard having a neck which snugly fits over the open end of the sample tube to form a substantially leakproof connection. The funnel shaped needle guard is provided, on its internal surface, with one or more vertical grooves and one or more circular grooves which channel any accidental spillage of the sample into the sample tube. The glass sample tube is coated with a resin which makes the tube shatterproof in the event it is accidentally dropped. By coating the glass tube with resin, the integrity of the tube is maintained and the sample contained within even though the tube is broken. This greatly reduces the risk of the spread of disease to health care personnel caused by accidental needlestick and spillage of samples.

DETAILED DESCRIPTION OF THE INVENTION

Figure 1:
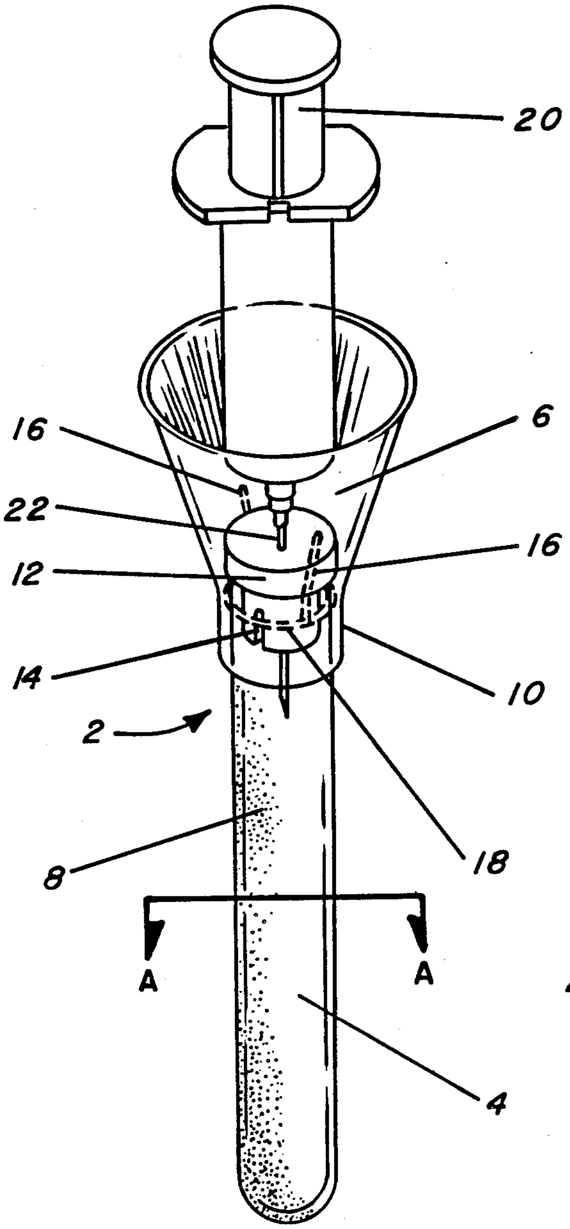
FIG. 1 is a perspective view of my medical safety device.
Figure 2:
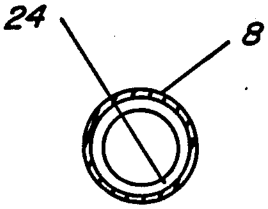
FIG. 2 is a partial cross-section along line A—A of FIG. 1.
Figure 3:
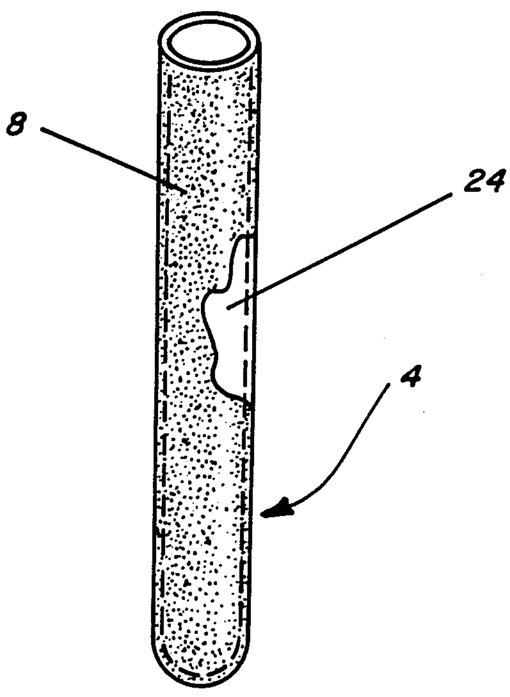
FIG. 3 is a perspective view of the safety sample tube of FIG. 1.
Figure 4:
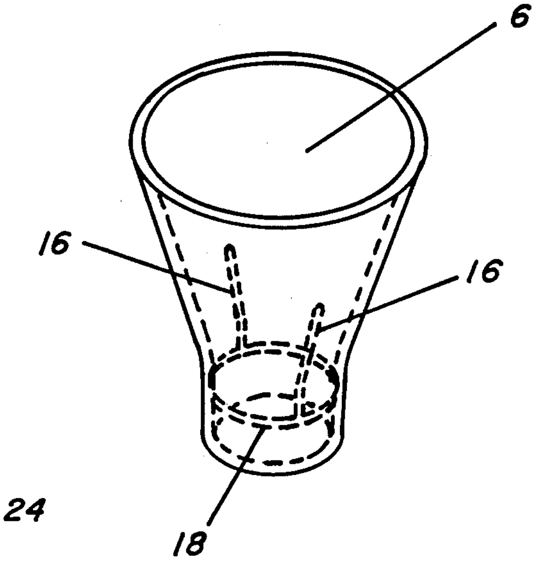
FIG. 4 is a perspective view of the safety needle guard of FIG. 1.

With reference to FIG. 1, the medical safety device 2 of the present invention comprises a sample tube such as vacuum tube 4 and a funnel shaped needle guard 6. The external surface of wall 24 of tube 4 is provided with a continuous thin coating of a resin as best shown in FIGS. 2 and 3. The resin 8 covers the exterior surace of the glass tube continuously and up to the lip thereof. The resin coating makes the sample tube substantially shatterproof so that in the event of accidental dropping of the sample tube, the sample remains intact even though the tube may be broken. The resin coating acts as an envelope to hold and contain the glass. Thus, spillage of the sample is prevented and risk of the spread of disease is reduced. The funnel shaped needle guard or hand guard 6 greatly reduces the risk of accidental needlestick and consequent exposure to the risk of transfer of disease to health care personnel. Thus, if the person taking the blood sample, for example, is fatigued or hurried, the wide upper opening of the guard 6 gives a good margin of safety for proper positioning of needle 22 of the hypodermic syringe 20 in the cap 12 to reduce the risk of accidental heedlestick. In the event of premature ejection of or excess of sample fluid from the syringe, vertical groove(s) 16 and circular groove(s) 18, which interconnect, are provided to safely drain or channel the premature discharge or excess into tube 4. When cap 12 is raised, the premature discharge or excess passes into the sample tube 4 via the cap groove 14 which is in communication with interconnecting grooves 16 and 18. In this way, spillage from syringe 20 is contained and the risk of transfer of disease is reduced. Cap 13 of the vacuum tube 4 is raised by putting upward pressure on guard 6. The internal radius of the guard at the juncture of the neck and the slanted funnel walls is narrower than the radius of the top of cap 12. Consequently, when guard 6 is removed upwardly, cap 12 is removed from the tube. This is another safety feature of the invention in that when the vacuum of the tube is broken, sometimes a mist or fine spray of the sample fluid is emitted. The guard effectively captures the mist and prevents it from contacting the person. In addition, to further reduce the risk of the spread of disease from accidental spillage of the blood sample or other body fluid, the needle guard neck 10 is snugly fitted or engaged with the resin surface 8 of sample tube 4. The needle guard is preferably made of resin and the contact or engagement of the inner surface of the neck thereof with the resin surface of the sample tube provides a substantially leakproof joint. In this way, accidental leakage of the fluid sample onto the health care person is substantially reduced. The radius of the upper opening of the guard 6 can be about 1.0 to 2.0 inches. The length of the guard neck 10 can be about 0.5 to 1.0 inch. The overall length of the guard can be about 1.0 to 2.0 inches.

Figure 5:
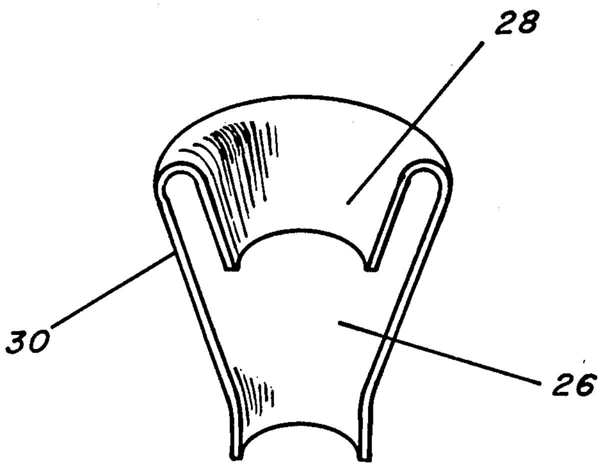
FIG. 5 is an elevational cross-section view of another embodiment of a safety needle guard in accordance with the present invention.

Referring to FIG. 5, another embodiment of the needle guard is shown. In that embodiment, the needle guard 26 is provided with an inwardly and downwardly extended lip 28 which is spaced inwardly from outer wall 30 to form a chamber into which any fluid spillage from the syringe or tube can collect in the event of accidental discharge of or dropping of the sample. This feature substantially reduces the risk of health care personnel contacting sample fluids which may carry disease. The needle guard 26, like guard 6, can be provided with grooves 16 and 18 on the inner surface for additional safety.

In the preferred practice of the invention, the needle guard of my invention is used in conjunction with the resin coated glass tube 4. Obviously, my needle guard can be used with uncoated tubes such as a vacuum tube as well. In either case, the guard is generally removed from the sample tube prior to putting the tube in a centrifuge.

The needle guard is preferably made by molding using either a thermoplastic or thermosetting resin. Suitable resins include polyethylene, polypropylene, polystyrene, polyvinyl chloride, ionomers, nylon, polyvinyl acetate and polyvinyl butyral.

The resin coated glass sample tube can be made by applying a coating of resin using a bed of fluidized resin powder and preheating and/or postheating the glass tube. Fluidized bed processes and resins described in U.S. Pat. Nos. 4,506,189. 3,856,498, 3,937,854 and 3,959,525, the disclosures of which are incorporated herein, are suitable. The resin coated glass sample tube can be made by vacuum forming a preformed thermoplastic sleeve onto the glass tube. Vacuum forming and resins described in U.S. Pat. No. 3,902,946, the disclosure of which is incorporated herein by reference, can be used in making the coated sample tube of the present invention. Another method of manufacture is to dip the glass sample tube into a solution or dispersion of resin followed by heating to set the resin. Suitable resin despersions and process conditions for this method are described in U.S. Pat. Nos. 2,868,670, 3,621,323 and 3,715,232, the disclosure of which are incorporated herein by reference. The thickness of the resin coating needed to prevent shattering of the glass tube can vary considerably in accordance with the resin. As a guide, the thickness of the resin coating can be within the range of about 0.008 to 0.020 inches in order to provide a shatterproof envelope. Preferably the resin coating is transparent or only slightly opaque so that visibility of the sample fluid in the tube is not blocked.

EXAMPLE

A moisture free preformed sleeve of polyethylene having a thickness of 0.015 inches is placed over a glass vacuum tube previously cleaned with acetone. The upper open end of the sleeve is in alignment with the lip of the tube. Heat is uniformly applied to the sleeve and tube until approximately the softening temperature of the polyethylene. Then vacuum is drawn to cause the polyethylene sleeve to be formed onto the glass vacuum tube until the interface therebetween is free of air voids or bubbles. The coated tube is allowed to cool at room temperature.

Suitable resins for preparing a resin coated glass sample tube in accordance with the present invention include, but are not limited to, polyethylene, polypropylene, polyvinyl chloride, ionomers (copolymers of an alpha olefina and an alpha, beta ethylenically unsat. carboxylic acid such as ethylene and methacrylic acid), silicones, polyvinyl butyral, polycarbonates, and the like. Preferably, the resin is a thermoplastic resin. Additives such as plasticizers, fillers, stabilizers, and the like can be included in the resin.

What is claimed is:

1. A medical safety device for body fluid samples which comprises:

a funnel shaped needle guard which is open at its upper end and lower end, said upper end being of a larger diameter than the lower end, said lower end forming a neck portion, the interior surface of the guard having one or more vertical grooves and one or more circular grooves which interconnect and provide for the passage of body fluid, and a resin coated glass sample tube having an upper open and a closed lower end receiving and holding a body fluid sample, the upper end of said tube being positioned within the neck of said needle guard, and said resin coated tube being characterized in that said coating is continuous and covers the exterior surface of the glass tube to make it substantially shatterproof.

2. The device according to claim 1 wherein the resin coated glass sample tube is a glass vacuum tube coated with a thermoplastic resin.

3. The device according to claim 2 wherein said interconnecting vertical and circular grooves of the needle guard are in communication with the groove in the cap of the vacuum tube so that any spillage of body fluid is channeled into the tube.

4. The device of claim 1 wherein said resin coated glass sample tube is a glass tube coated with a thermoplastic resin.

5. The device of claim 1 wherein said needle guard is made of a thermoplastic resin.

* * * * *